(12) United States Patent
Ozkan et al.

(10) Patent No.: US 6,605,453 B2
(45) Date of Patent: Aug. 12, 2003

(54) ELECTRIC-FIELD-ASSISTED FLUIDIC ASSEMBLY OF INORGANIC AND ORGANIC MATERIALS, MOLECULES AND LIKE SMALL THINGS INCLUDING LIVING CELLS

(75) Inventors: Mihrimah Ozkan, La Jolla, CA (US); Sadik Esener, La Jolla, CA (US); Sangeeta Bhatia, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/728,801

(22) Filed: Dec. 1, 2000

(65) Prior Publication Data

US 2002/0031813 A1 Mar. 14, 2002

Related U.S. Application Data

(60) Provisional application No. 60/168,779, filed on Dec. 1, 1999.

(51) Int. Cl.$^7$ .......................... C12N 13/00; B05D 1/06; C25D 15/00
(52) U.S. Cl. .................... 435/173.1; 427/469; 204/471; 204/484
(58) Field of Search ...................... 435/173.1; 427/469; 204/484, 471

(56) References Cited

U.S. PATENT DOCUMENTS

| | | | | |
|---|---|---|---|---|
| 4,661,451 A | * | 4/1987 | Hansen ........................ | 204/403 |
| 5,605,662 A | * | 2/1997 | Heller et al. ................. | 204/600 |
| 5,750,015 A | * | 5/1998 | Soane et al. ................. | 204/451 |
| 5,795,457 A | * | 8/1998 | Pethig et al. ................ | 204/547 |
| 5,855,753 A | * | 1/1999 | Trau et al. .................... | 204/484 |
| 6,051,422 A | * | 4/2000 | Kovacs et al. ............... | 204/403 |
| 6,071,394 A | * | 6/2000 | Cheng et al. ................ | 204/547 |

FOREIGN PATENT DOCUMENTS

WO   WO-0140786 A1 * 6/2000

OTHER PUBLICATIONS

Cheng et al., "Preparation and Hybridization Analysis of DNA/RNA from *E. coli* on Microfabricated Bioelectronic Chips" (1998) Nature Biotechnology, vol. 16(6), 541–546.*

* cited by examiner

*Primary Examiner*—Jon P. Weber
(74) *Attorney, Agent, or Firm*—Fuess & Davidenas

(57) ABSTRACT

Any of inorganic and bio-organic substances and molecules, and beads, pucks and like small things, that are both (i) electrically charged to a first polarity, and (ii) immersed in a fluid transport medium within (iii) an electrochemical cell, are assembled and patterned by action of moving these inorganic and bio-organic substances and molecules, etc. to a patterned electrode having an opposite, second, polarity under force of an applied electric field. The electrode patterned with conductive areas may be further, separately, patterned with chemicals, for example agarose gel, that chemically accept or reject the substances and molecules, etc., especially as are biological in origin. Living cells of plant, bacterial and animal types may be assembled. A semiconductor electrode may be patterned by masked laser light passed through the other electrode, which is transparent.

17 Claims, 4 Drawing Sheets

- SMALL THINGS 20
- Si SUBSTRATE
- TIO GLASS
- AL PLATE
- RUBBER GASKET
- SOLUTION 21

1) MASK
2) SPIN ON PHOTORESIST
3) SPIN ON AGAROSE GEL
4) SILICON SUBSTRATE

PATTERNED AGAROSE GEL

SUBSTRATE A

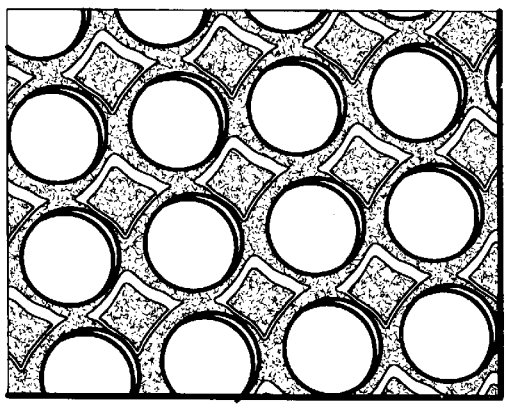
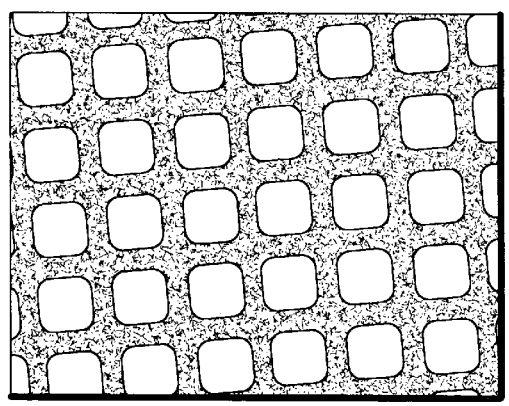
FIG. 10A                    FIG. 10B
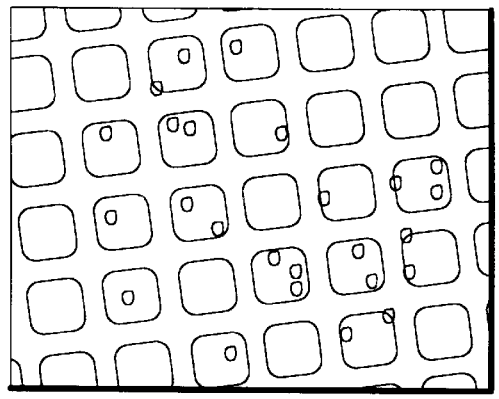
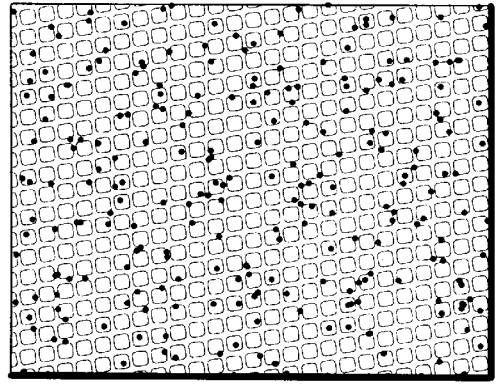
FIG. 11A                    FIG. 11B
TOP VIEW 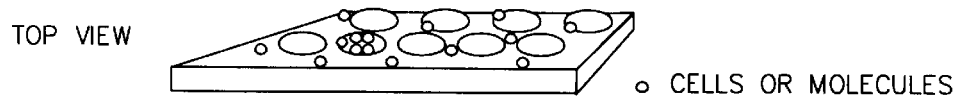 ○ CELLS OR MOLECULES
FIG. 12A
BACK VIEW 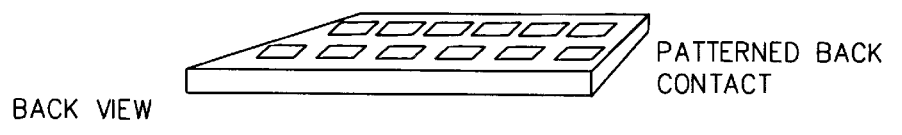 PATTERNED BACK CONTACT
FIG. 12B

ELECTRIC-FIELD-ASSISTED FLUIDIC ASSEMBLY OF INORGANIC AND ORGANIC MATERIALS, MOLECULES AND LIKE SMALL THINGS INCLUDING LIVING CELLS

RELATION TO A PROVISIONAL PATENT APPLICATION

The present patent application is descended from, and claims benefit of priority of, U.S. provisional patent application Serial No. 60/168,779 filed on Dec. 1, 1999, for FIELD-ASSISTED FLUIDIC ASSEMBLY OF INORGANIC AND ORGANIC DEVICES, MATERIALS AND MOLECULES, which provisional patent application is to the selfsame inventors as the present application.

This invention was made by support of the U.S. Government under Grant Number: MDA 972-98-1-0001 acting through the DARPA Heterogeneous Optoelectronic Technology Center. The U.S. Government has certain rights in this invention.

BACKGROUND OF THE INVENTION

1. Field of the Invention

The present invention generally concerns the assembly of (i) any of inorganic substances, molecules, beads, pucks, microspheres and like small things, and also (ii) biological organic (bio-organic) biomolecules, cellular structures, cells and like small biological structures; most typically into patterns on substrates.

Assembly of inorganic molecules may be, by example and not by way of limitation, for the fabrication of large array displays, for massively parallel III–V and II–VI device integration on a different mother substrates, and for heterogeneous integration and pick and place of electronic and/or opto-electronic devices.

Assembly of organic molecules may be, by example and not by way of limitation, for purposes of cell-based biosensors, drug discovery, pharmacogenomics, functional genomics, high-throughput phenotyping, in vitro biology (combinatorial cell culture, signal transduction mechanisms), or any application requiring massive organization of biological cells of any of the plant, bacterial or animal (including mammalian) types.

The present invention particularly concerns the large-scale biocompatible assembly of diverse inorganic and organic materials and molecules having a large range of sizes (typically 100 $\mu$m-20 microns) at high yield (~100%) over but short times (a few seconds) at massive parallelism (for example, so as to realize an array of >1000×1000 dimension).

2. Description of the Prior Art

The present invention will be seen to involve fluidic-based assembly and/or patterning of small objects, including biological cells, by the combinatorial use of (1) DC electric fields (in an electrical process) in an electrochemical cell having (2) electrodes (2a) at least one of which is selectively patterned (in an optical process), or (2b) at least one of which is selectively patterned by laser light (again in an optical process) where the small objects patterned to one of the (2) electrodes by action of the (ii) DC electric field commonly adhere to the electrode by chemical binding (a chemical process). The present invention will thus be seen to involve each of (1) electrical, (2) optical and (3) chemical processes.

This multi-process, or multi-dimensional, aspect of the present invention is not known to have previously existed, although the individual processes are relatively conventional, and proven.

2.1 Existing Art For Biological Applications

Electrokinetic methods of manipulating cells are described by D. J. Harrison, et al., of Caliper, Inc.

Each of (i) dielectrophoresis, or the manipulating of cells with alternating current fields, (ii) physical methods of localizing molecules and cells (e.g., microfluidics), and (iii) chemical methods of localization (self-assembled monolayers and other specific chemical modifications) are also known in the art.

2.2 Existing Art For Non-Biological Applications

Each of (i) robotic pick and place, (ii) fluidic self assembly, (iii) flip chip bonding, and (iv) probe force microscopy is an established method of manipulating and assembling various small non-organic structures.

2.3 Non-Contact Manipulation

The present invention will be seen to permit non-contact manipulation of small things.

A previous system and method permitting non-contact manipulation of microparticles is shown in U.S. Pat. No. 6,055,859 to Mitome and Tuziuti, and assigned to the Agency Ministry of International Trade and Industry, Tokyo, Japan. This patent for a NON-CONTACT MICROMANIPULATION METHOD AND APPARATUS concerns a method of non-contact micromanipulation using ultrasound. In the method micro particles are distributed in a liquid medium. A ultrasound transducer has a transducer plate, with a surface electrode wholly covering a first principal surface of the transducer plate and with a reverse surface electrode on a second principal surface of the transducer plate. The electrode has a number of short electrode strips arranged in parallel. A reflector is set spaced-parallel in opposition to the first principal surface of the transducer plate at a prescribed distance. A voltage is applied to at least one electrode strip so as to radiate ultrasound, forming a standing wave field between the ultrasound transducer and the reflector which traps the micro particles. The voltage applied to the selected electrode strip is switched to an adjacent electrode strip so as to move the standing wave field by moving the position of ultrasound radiated by the ultrasound transducer, therein moving the trapped micro particles in a direction in which the electrode strips are arrayed.

SUMMARY OF THE INVENTION

The present invention contemplates a photo-electrochemical (or, to use an alternative word, an opto-electrochemical) system and method for patterning and assembling of (i) any of inorganic substances, molecules, beads, pucks, microspheres and like small things, and also (ii) biological organic (bio-organic) biomolecules, cellular structures, cells and like small biological structures—including as may be alive. (For purposes of the present invention, "small" shall mean less than 20 microns in size.) The manipulatable cells include, without limitation by way of lack of enumeration, cells of the plant, bacterial and animal, including mammalian animal, types.

The system and method of the present invention may still further alternatively be described—albeit arguably less suitably—as "electro photo-chemical" or even "chemical photo-electric", system and method. The main concept is simply that each of (1) electrical, and (2) chemical, and (3) photo, or optical, processes are variously involved in the invention. In the invention each of these processes (1)–(3) is expressed in an electrochemical, or optoelectrochemical, "cell" of many centimeters size, in which "cell" the overall method of the present invention is conducted. This cell normally, and preferably, consists of (i) two spaced-parallel planar electrodes, one of which electrodes is sometimes transparent (e.g., ITO glass) separated by (ii) a dielectric fluid containing the inorganic or bio-organic substances and molecules, etc., that are desired to be patterned upon one of the electrodes.

The (1) electrical process transpiring within the cell is perhaps the simplest. Inorganic and bio-organic substances and molecules, and beads, pucks and like small things that are both (i) electrically charged to a first polarity, and (ii) immersed in a fluid transport medium, are patterned by action of moving these inorganic and bio-organic substances and molecules, and beads, pucks and like small things to a patterned electrode of an opposite, second, polarity under force of an applied electric field. Upon first consideration, it seems as if the process of assembling the inorganic and bio-organic substances and molecules, etc., is finished already, there not being much need to consider (2) chemistry nor (3) optics.

However, one or more (2) chemical processes transpiring within the cell can also be important. In the first place, the fluid transport medium is desirably biocompatible, may even be a nutrient solution, when the moved (and patterned) items are bio-organic molecules or cells, including living cells of any of the plant, bacterial or animal types. Secondly, when the patterned materials are organic then, in order to enhance patterning selectivity and efficiency, it is often useful that the patterned electrode should be so patterned not only so as to selectively create electrically conductive regions, but also so as to selectively chemically bind biomolecules. In other words, the electrodes are patterned twice: once with electrically conductive regions and once with chemically receptive (or repulsive) regions. The patterned regions may, or may not, be the same.

For example, agarose gel, as a material broadly non-receptive to biomolecules, may be patterned in, for example, all regions of the electrode except the conductive regions. Moreover—and similarly to this selective patterning with agarose gel of an electrode that is already patterned with conductive regions—an electrode that patterned into conductive regions may be further patterned (or re-patterned) in all its regions with still further chemicals so as to selectively accept and bind, or to reject, material that comes, by force of an applied electric field or otherwise, into contact with (patterned) electrode regions, and/or with other regions.

In simplest terms, the (2) chemical processes of the present invention make, insofar as is possible, that the desired material (the inorganic and bio-organic substances and molecules, etc.) within the fluid transport medium will, once transported under force of an electric field between patterned electrodes to desired locations, and only to desired locations, stay in these locations, and only these desired locations, for so long as desired, and only for so long as desired. Differently chemically patterned regions on the electrode may accept, and reject, various of the inorganic and bio-organic substances and molecules, etc. that are all within the fluid transport medium at the same time, or which are within different aliquots of the fluid transport medium successively applied (in a multi-step assembly method). The electrochemical cell with its (1) electrical and (2) chemical processes is sufficient to rapidly (a few seconds per process) reliably (~100% yield) fabricate from very small objects (typically 100 $\mu$m-20 microns) a complete, and permanent, device having high complexity (in accordance with the patterning of the electrode) and massive parallelism (for example, an array of >1000×1000 dimension).

Involvement of the final (3) photo, or optical, process in the method and system of the present invention comes in two forms. In a more rudimentary and conventional form, photo processes may be used to pattern the conductive regions of the electrode, as by the photolithographic patterning of a photoresist subsequently followed by etching. The same photo processes may also be conventionally used to pattern any chemicals, such as agarose gel, that are applied to the electrode.

In another, optional, use of photo, or optical, processes, however, the present invention contemplates dynamically photo-patterning a photosensitive electrode (which may or may not be pre-patterned with (i) selected electrode regions, and/or with (ii) selected chemical regions) before, or even during, the process of electrochemical deposition. This photo-patterning of a photosensitive electrode, which is preferably made from semiconductor, preferably transpires by passing masked laser light through the other, spaced-parallel, electrode which is transparent, and which is preferably constructed from ITO glass. The photo-patterning, and re-patterning, transpires before each time(s) of, or even during, the electrochemical migration (under force of the applied electric field) of the inorganic or bio-organic substances and molecules, etc. In other words, the inorganic or bio-organic substances and molecules, etc., are patterned to an electrode that is itself dynamically photo-patterned (and/or re-photo-patterned).

This photo-patterning, and dynamic photo-patterning, of a "template" electrode to which micro-assembly will be make is, it is respectfully suggested, a powerful concept. When this concept is further coupled with the selective chemical patterning of the electrodes, the present invention offers a powerful method and system for the multi-step assembly of complex objects, including as may contain biomolecules and living cells.

In detail, the photo-patterning is in accordance with the present invention is preferably realized by printing, or patterning, an electrode with laser light. The electrode is preferably so patterned through, and while already assembled spaced-parallel with, another, transparent, electrode; the two electrodes together forming a cell. An appropriate fluid containing appropriate inorganic or bio-organic substances and molecules, etc., is entered between the electrodes; an electrical field is applied; and desired inorganic or bio-organic substances and molecules, etc. are patterned on and to the photo-patterned electrode. The whole process may then be repeated for any of new patterns, solutions, inorganic or bio-organic substances and molecules, etc. Clearly a complex device may be constructed by sequential processes which may be automated and computer-controlled.

1. A Method of Assembling any of Inorganic and Bio-organic Substances and Molecules, and Beads, Pucks and Like Small Things Accordingly, in one of its aspects the present invention is embodied in a method of assembling any of inorganic and bio-organic substances and molecules, and beads, pucks and like small things, that are capable of holding an electrical charge.

The method consists of patterning any of these inorganic and bio-organic substances and molecules, etc., that are both (i) electrically charged to a first polarity, and (ii) immersed in a fluid transport medium, by act of moving under force of an applied electric field these inorganic and bio-organic substances and molecules, etc. to a patterned electrode having an opposite, second, polarity. The inorganic and bio-organic substances and molecules, etc. accumulate on, and assume the pattern of, the patterned electrode.

The patterning may be of bio-organic substances and molecules, etc. that are negatively charged while the patterned electrode is positively charged, or vice versa.

The patterned bio-organic substances and molecules may, in particular, be any of biological cells of at least the plant, bacterial and animal (including mammalian animal) types, biological molecules including proteins, and/or DNA.

The patterning may be of bio-organic substances and molecules that are alive, in which case the fluid transport medium is bio-compatible.

2. The Assembly Method Extended to Patterning the Electrode Both for (i) Conductive and Non-Conductive Regions, and (ii) Regions of Affinity, or Non-affinity, to Bio-organic Substances, Molecules and/or Cells In another of its aspects the method of the present invention set forth in section 1 above may be expanded and extended to—at a time and as a step before the patterning of any of inorganic and bio-organic substances and molecules, etc.—patterning the electrode with either or both (i) conductive regions, and/or (ii) chemically receptive or rejecting regions.

Patterning the electrode with conductive regions is preferably conventionally realized by photolithographically pre-patterning a semiconductor electrode with an insulator so that the electrode assumes selected conductive and insulating regions.

This pre-patterning directed to creation of conductive and non-conductive electrode regions may itself be expanded and extended by, at a time and as a step before the photolithographically pre-patterning, further pre-patterning regions of affinity, or non-affinity, to bio-organic substances, molecules and/or cells. This further pre-patterning preferably consists of coating the electrode with a non-stick substance to which bio-organic substances, molecules and/ or cells subsequently applied in the patterning step will not stick. (It is alternatively possible to coat the electrode with a substance to which bio-organic substances will stick, or bind.) By this step the photolithographic pre-patterning will also pattern the nonstick substance, leaving an electrode with regions that are selectively receptive, or non-receptive, to bio-organic substances, molecules and/or cells.

The coating of the semiconductor electrode is preferably with agarose gel. Where remaining in non-conductive regions of the electrode after the photolithographic pre-patterning, this agarose gel will cause that bio-organic substances, molecules and/or cells will not stick to these non-conductive regions, which is beneficial for the efficiency and the selectivity of the ultimate electrochemical patterning of these bio-organic substances, molecules and/or cells into, and on, the conductive regions (only).

3. The Assembly Method Still Further Extended to Photo-Patterning (and Re-Photo-Patterning) the Electrode In yet another of its aspects the method of the present invention set forth in section 1 above may be still further expanded and extended to photo-patterning (and re-photo-patterning) the electrode.

In this variant of the method a cell has a first electrode which is transparent spaced-parallel to a second electrode— which will second electrode become the patterned electrode—that is photosensitive. The preferred photosensitive electrode is a semiconductor.

The photosensitive second electrode may be photo-patterned at a time, and as a step, before any patterning of any inorganic and bio-organic substances and molecules, and beads, pucks and like small things. However, the second electrode may also be photo-patterned during the electrochemical deposition.

A light source like a laser is shined through a mask. The laser light generates electrons and holes on exposed regions of the photosensitive electrode. As a result there will be a larger anodic current in these regions. The excess current of these regions selectively drives negatively charged biological cells, molecules or like small things to these regions. When a patterned mask is used, bio-molecules/devices within the solution will move towards the illuminated on the photosensitive electrode.

In detail, the semiconductor second electrode is preferably photo-patterned (and re-photo-patterned) by selectively exposing it through the transparent first electrode with masked radiation, therein serving to pattern the photosensitive electrode into (i) one or more first regions that are electrically charged to the first electrical polarity and (ii) one or more second regions that are oppositely charged to the second electrical polarity. By this photo-patterning, the subsequent, or concurrent, movement in the electrochemical cell of the inorganic and bio-organic substances and molecules, and beads, pucks and like small things (that are electrically charged to the first electrical polarity) will cause these inorganic and bio-organic substances and molecules, etc. to be attracted to the second region of the patterned photosensitive electrode.

4. An Electrochemical Cell for Assembling Any of Inorganic and Bio-organic Substances and Molecules, and Beads, Pucks and Like Small Things That are Capable of Holding an Electrical Charge In still yet another of its aspects the present invention may be considered to be embodied in an electrochemical cell for assembling any of inorganic and bio-organic substances and molecules, and beads, pucks and like small things that are capable of holding an electrical charge.

The cell preferably includes a patterned first electrode spaced apart from, and more preferably spaced parallel to, a second electrode by an insulator. A reservoir space formed between the two spaced-apart electrodes contains a solution containing any of inorganic and bio-organic substances and molecules, and beads, pucks and like small things having an electrical charge of a first polarity.

A generator creates an electrical potential between the first and the second electrode, and thus a commensurate electrical field within the solution.

If the patterned first electrode assumes an electrical charge of a second polarity then any of the electrically-charged inorganic and bio-organic substances and molecules, and beads, pucks and like small things that are charged to the first polarity and that are within the solution will migrate towards the first electrode, assuming the pattern thereof.

The patterned first electrode is preferably a semiconductor, and is more preferably silicon.

The second electrode is preferably ITO coated glass.

The insulator is preferably a rubber gasket.

These and other aspects and attributes of the present invention will become increasingly clear upon reference to the following drawings and accompanying specification.

BRIEF DESCRIPTION OF THE DRAWINGS

Referring particularly to the drawings for the purpose of illustration only and not to limit the scope of the invention in any way, these illustrations follow:

FIG. 3a shows agarose patterning on a substrate or one electrode of the electrochemical cell while

FIG. 4a shows a random baseline distribution of 10 μm polystyrene beads on a patterned electrode substrate at 0 v.d.c. while

FIGS. 10a and 10b show patterned agarose gel on silicon chip; in FIG. 10a agarose covers the insulator area only while in FIG. 10b agarose is patterned directly on a blank silicon.

FIGS. 11a and 11b show biological cell patterning by using electric field and agarose patterned substrate together within the electrochemical cell of the present invention.

FIG. 12a shows a patterned back contact on the electrochemical cell of the present invention, and FIG. 12b shows the effect of this patterned back contact on the localized patterning of organic cells or molecules.

DESCRIPTION OF THE PREFERRED EMBODIMENT

The following description is of the best mode presently contemplated for the carrying out of the invention. This description is made for the purpose of illustrating the general principles of the invention, and is not to be taken in a limiting sense. The scope of the invention is best determined by reference to the appended claims.

1. Preparation of the Electrochemical Cell: "Electrical Addressing"

Figure 1:
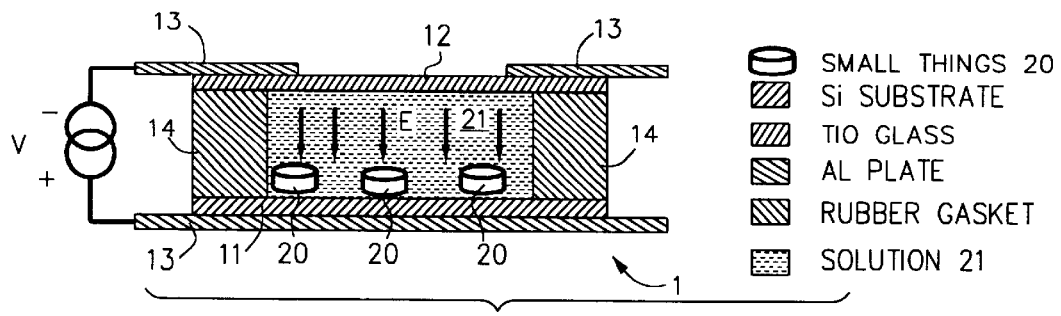
FIG. 1 shows a schematic representation of the proposed electrochemical cell.

A schematic representation of a preferred electrochemical cell 1 of the present invention is shown in FIG. 1. Referring to FIG. 1, in the electrochemical cell 1 two electrodes 11, 12 are connected by (i) a solution 21 containing (ii) inorganic or bio-organic molecules and like small things 20. By application of an electrical field E between two electrodes 11, 12 the inorganic or bio-organic molecules or things 20 that are charged are attracted to the electrode 11 of opposite charge.

In a preferred embodiment (1) ITO glass and (2) a semiconductor, preferably silicon, are respectively used as electrodes 12, 11. However the present invention works satisfactorily with other types of electrodes as well.

In detail, a silicon substrate is placed on a horizontal aluminum plate 13, thereafter to serve as a "bottom" electrode 11. ITO coated glass is placed spaced-parallel as a "top" electrode 12.

The two electrodes 11, 12 are preferably both (i) electrically isolated, and (ii) the device/bio-organic molecule containing fluid solution 21 between them contained, by use of a flat rubber gasket 14 in the shape of a closed loop.

A liquid medium, or mixed media, solution 21 containing biological micro-structures or cells—the small things 20—is placed between the electrodes 11, 12. In order to create electric field E between the electrodes 11, 12, and inside the liquid medium, a potential V is applied between the electrodes 11, 12. The cells, or other small things 20, are negatively charged they are attracted to the positively charged electrode 11. With a patterned substrate electrode 11, selective spatial distribution of the cells or other small things 20 is possible.

2. Preparation of the Photo-electrochemical cell: "Optical Addressing"

Figure 2:
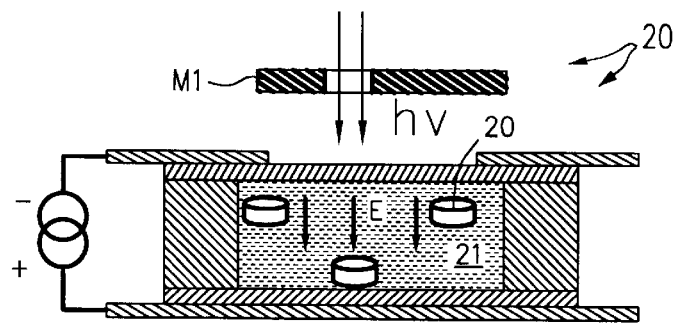
FIG. 2 is a schematic representation of the opto-electrochemical system in accordance with the present invention.

By addition of a photosensitive substrate into the same electrochemical cell 1 described above can be used for opto-electrical addressing of the biological cells, molecules or charged devices. A schematic representation of a preferred opto-electrochemical system 2 in accordance with the present invention is shown in FIG. 2.

A light source like a laser (not shown) is shined through a mask M1. This laser light hv will generate electrons and holes on the semiconductor substrate, or electrode 11. As a result there will be a larger anodic current on this substrate, or electrode 11. These excess current regions will drive negatively charged biological cells, molecules or other small things 20. With this scheme if a patterned mask M1 is used, then bio-molecules/things 20 within the solution 21 will move towards the illuminated regions on the photosensitive substrate, or electrode 11.

This variant electrochemical cell provides another method of localizing fields—enabling independence from fluid contact, selection of a particular cell or particle, and, in essence, creating an 'interactive surface' with the user.

3. Substrate Preparation

In that preferred embodiment of an electrochemical cell 1 in accordance with the present invention previously seen in FIG. 1 the silicon electrode substrate, or electrode 11, is preferably patterned with an insulator. Different semiconductor (or metal) and dielectric material combinations are possible. One preferred combination is Si and SiN.

Figure 3A:
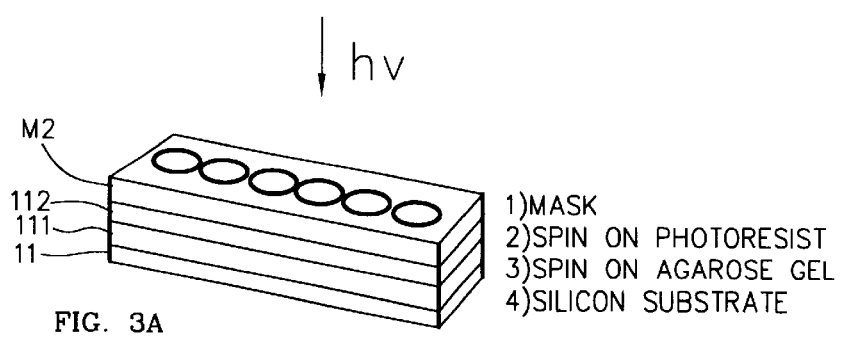
Figure 3B:
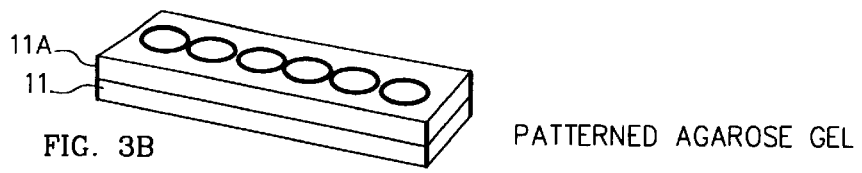
FIG. 3b shows the electrochemical cell patterned on one electrode with agarose gel.

The electrode 11 may also be patterned with one or more chemicals accepting, or rejecting, one or more of the molecules or things 20, including living cells, that are within the liquid medium 21. The manner of so doing is diagrammatically illustrated in FIG. 3: FIG. 3a showing the stepwise patterning of a chemical 111 on a substrate, or one electrode, of the electrochemical cell 1—illustrated to be electrode 11—while FIG. 3b shows the electrochemical cell 1 now patterned on its electrode 11 with the chemical 111a. An exemplary preferred chemical 111, 11a is agarose gel.

As illustrated in FIG. 3a, in order to prevent possible bio-cell adhesion agarose gel 111 is spin on the electrode substrate 11 and a thick photoresist 102 is spin on the top of the agarose gel 111. The electrode 11 substrate is then hard baked at 90° C. for two hours. By using conventional lithography technique, the photoresist 112 is patterned by mask M2. After this patterning of the photoresist 112 the electrode 11 substrate is etched in an oxygen plasma chamber (not shown). Agarose 111 is etched down where there is no photoresist 112 protection, becoming patterned agarose 111a. FIG. 3 shows a schematic representation of this agarose, or chemical, patterning in accordance with the present invention.

For any patterning of inorganic things there is no need for agarose layer on the insulator, agarose being of utility where bio-molecules are involved. However, some small inorganic things may have chemical affinities, and the pre-patterning of the electrode 11 like as the electrode 11 patterning with the agarose gel 111a may beneficially be used to prepare the substrate 11 for the ultimate assembly, within the electrochemical cell 1, of these small inorganic things.

4. Operation of the Preferred System of the Invention

After agarose gel 112 is patterned on the substrate, or electrode 11, this electrode 11 is used as an anode in the electrochemical cell 1 described in section 2 above, and shown in FIG. 1. Cells or other small things 20 are released in a solution 21 into the chamber between the electrodes 11, 12. An electric field E is applied between the electrodes 11, 12. Since the patterned substrate of electrode 11 is positively polarized, negatively charged biological cells are attracted to the patterned electrode surfaces. Since biological cells won't stick to the agarose gel 111a, this improves the efficiency of the biological cell patterning. Similar experiment is repeated for DNA molecule in deionized water solution. This time there is no need for an agarose patterned substrate.

For application in assembling inorganic devices, charged beads and dummy pucks are attracted to the oppositely charged electrode (i.e., electrode 11, being the anode) by the applied electric field E. Again, there is no need for agarose coating for this purpose.

5. Application of the Invention for the Assembly of Charged Beads, Pucks, LEDs and the Like on a Substrate so as to Make Devices Many different combinations of electrodes 11, 12 are possible. For example, Si/SiN may be used for the patterned electrode 11 substrate, and ITO glass for the other electrode 12. Polystyrene beads in 0.8 $\mu$m, 10 $\mu$m, 20 $\mu$m diameter were patterned on the substrate. Dummy $SiO_2$ pucks of 50 $\mu$m and 100 $\mu$m diameter, and LEDs of 50 $\mu$m diameter LED, were also patterned similar fashion.

FIGS. 4, 5, 6 and 7 show the results of these patternings and assemblies.

Under application of positive bias to the substrate electrode 11, negatively charged beads/pucks/devices were attracted to this electrode 11. However when a negative bias was applied to the same electrode 11, the similar charged beads/pucks/devices were rejected from the surface of electrode 11.

Figure 4A:
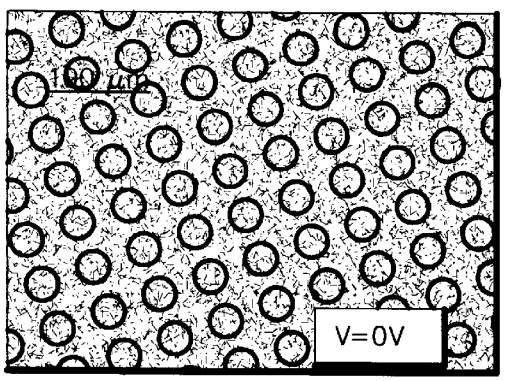
Figure 4B:
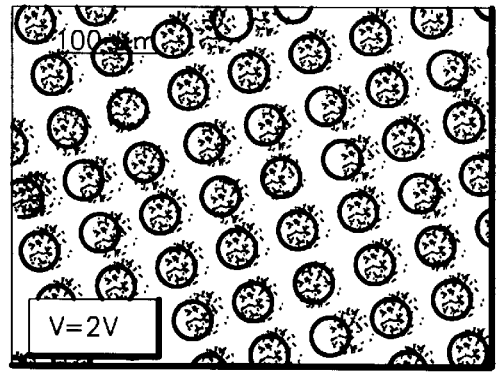
FIG. 4b shows patterned beads on the same electrode substrate after application of 2 v.d.c.

A random baseline distribution of 10 $\mu$m polystyrene beads on a patterned substrate at 0 v.d.c. is shown in FIG. 4a. Patterned beads on the same substrate after the application of 2 v.d.c. is shown in FIG. 4b.

Figure 5A:
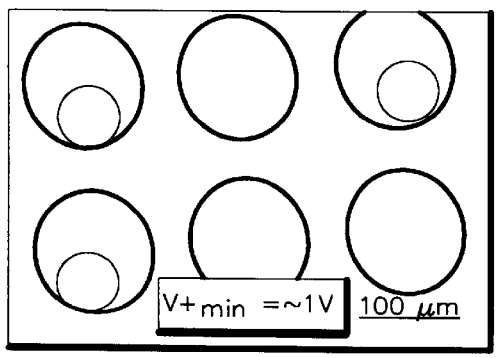
FIGS. 5a and 5b show attracted and rejected 50 μm $SiO_2$ pucks on the patterned electrode substrate with applied 1 v.d.c. and −2 v.d.c, respectively.
Figure 5B:
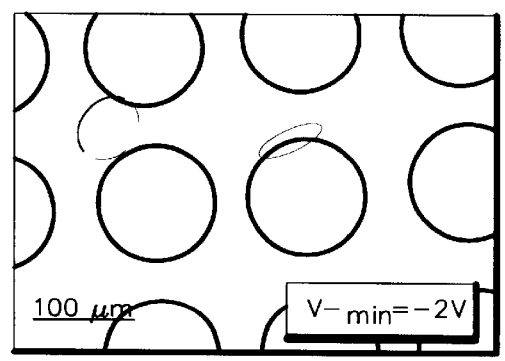

Attracted and rejected 50 $\mu$m $SiO_2$ pucks on the patterned electrode substrate with applied 1 v.d.c. is shown in FIG. 5a, and with −2 v.d.c. in FIG. 5b.

Figure 6A:
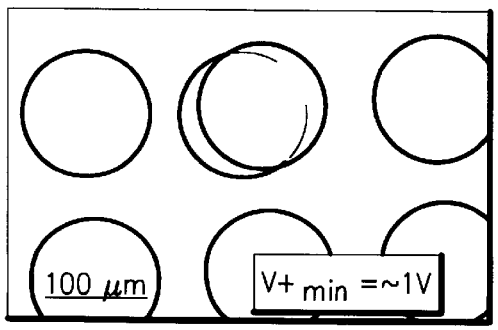
FIGS. 6a and 6b show attracted and rejected 100 μm $SiO_2$ pucks on the patterned electrode substrate with applied 1 v.d.c. and −3 v.d.c., respectively.
Figure 6B:
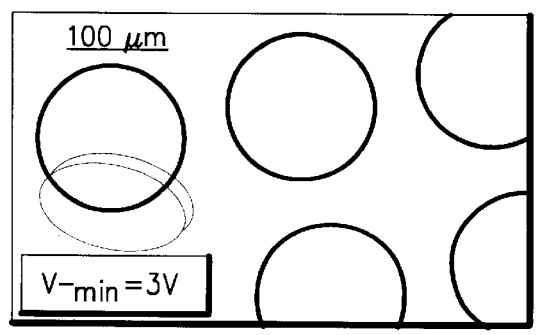

Attracted and rejected 100 $\mu$m $SiO_2$ pucks on the patterned substrate with applied 1 v.d.c. is shown in FIG. 6a, and with −3 v.d.c. in FIG. 6b.

Figure 7A:
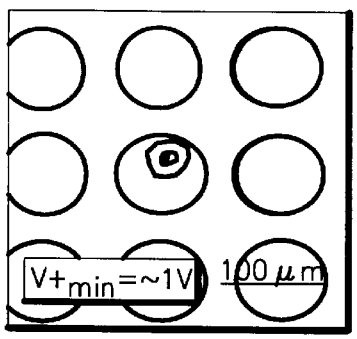
FIGS. 7a and 7b show attracted and rejected 50 μm LEDs on the patterned electrode substrate with applied 1 v.d.c. and −4 v.d.c., respectively.
Figure 7B:
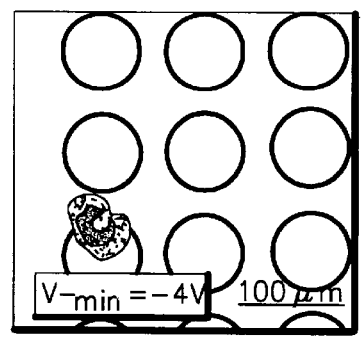

Attracted and rejected 50 $\mu$m LED on the patterned substrate with applied 1 v.d.c. is shown in FIG. 7a, and with −4 v.d.c. in FIG. 7b.

5. Application of the Invention for the Assembly of Charged Bio-organic Molecules, Cellular Components, Cells and the Like on a Substrate so as to Make Macro-biological Devices Bio-organic molecule and bio-cell patterning in accordance with the present invention can replicate the patterns of DNA molecules previously made elsewhere by other means.

Figure 8A:
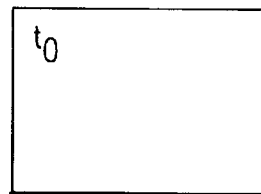
FIGS. 8a through 8c respectively show fluorescent tagged DNA patterning on Si/SiN patterned substrate at 0 v.d.c., 2 v.d.c. , and 4 v.d.c. potentials.
Figure 8B:
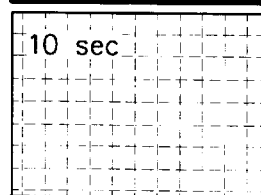
Figure 8C:
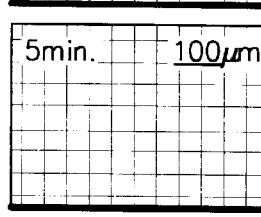

In particular, an a silicon nitride patterned silicon substrate, Texas red fluorescent tagged synthetic single strand DNA with 19 mer (sequence: 5'-CGT-AGA-ACT-CCT-CAT-CTC-CX-3' in deionized water) was patterned with applied electric field. Since DNA is negatively charged in nature it are attracted to the positively charged electrode surface. FIG. 4 shows the results of this process. The areas in the pictures represent a higher fluorescence due to higher concentration of DNA molecules at those regions. Fluorescent tagged DNA patterning on the Si/SiN patterned substrate is illustrated in FIG. 8. As the figure shows, DNA molecules are patterned across the substrate.

6. Application of the Invention for the Patterning of Biological Cells and Bio-organic Molecules (e.g., DNA, Proteins)

In accordance with the present invention, the patterning of biomolecules and inorganic particles to live cells has been achieved by manipulating the fluidic environment and electrode composition. To repeat, the patterning and assembly realized by the present invention is to live cells—a nontrivial extension of the art.

The first step in patterning biomolecules and inorganic particles to live cells is selection of the medium, or media. Cells cannot survive in deionized water as in the case of DNA molecules. Cell media has to be adjusted to physiologic cell osmolarity and pH. In addition, the cell solution must contain nutrients, ions, and other small molecules to remain viable. Since cell media is typically rich in salt, sugar and other substances, this makes the transport of cells difficult in the electrochemical chamber (due to shielding of charged species).

After trials on several different fluidic environments that are known to be biocompatible including sucrose, phosphate buffered saline and Kreb's Ringers Buffer (KRB), KRB was found optimal, and is preferred. Selection may be empirically made among a broad range of biocompatible and/or nutrient solutions on the basis of their resistivity and biocompatibility so as to optimize localization speeds, field strength, and other critical parameters of the system and method of the present invention.

In a first exercise of the system and method of the present invention to pattern live cells, some 70% of the cells placed into the solution KRB medium were successfully patterned on the electrodes. However there was still some non-selective attachment of cells on the insulator. After the cells adhere to the insulator surface, they could not readily be rendered mobile under the influence of an applied electric field. This effect can seen in FIG. 9 where the patterning cells with an applied electric field is shown. Notice the misplacement of cells on the insulator as well as patterning of cells on the electrode areas. In this exercise an Au-patterned silicon substrate was used.

Figure 9A:
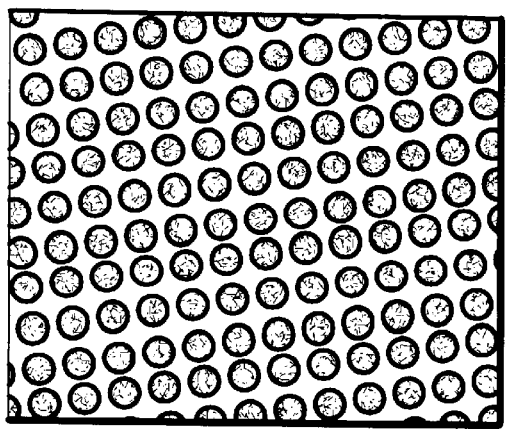
FIGS. 9a and 9b show patterned cells with an applied electric field.
Figure 9B:
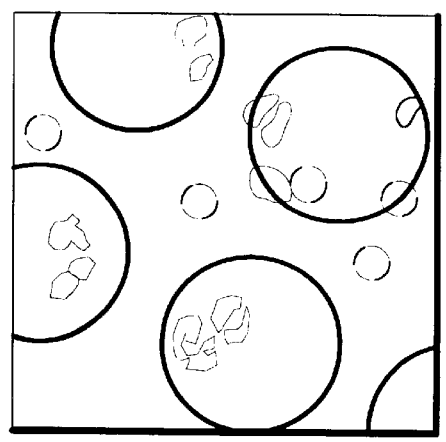

By assessment of FIG. 9, a "sticking" problem was noted. Cells were found to be sticking to the insulator as well as to the electrodes. This "sticking" makes quality patterning difficult even under electric field. In order to prevent this "sticking", agarose gel was spin on the substrate and patterned. It was then observed that cells would not stick to agarose gel as much as they do to the insulator surface. The patterned agarose on a blank of silicon and nitride (patterned on silicon substrate) is shown in FIGS. 10a and 10b. In FIG. 10a the agarose gel is shown patterned on silicon chip so as to cover the insulator area only. In FIG. 10b the agarose is patterned directly onto a blank of silicon.

Patterned agarose substrate and selected media is used with the proposed electrochemical system. FIG. 11 shows a picture of the fiberblast type of live biological cells. Cells are patterned by using this proposed technique. The yield is improved with agarose patterning. Cells positioned themselves within the electrodes away from the agarose coated surfaces. This also shows that if agarose is patterned on the nitride regions, the same effect will be obtained.

The patterning of biological cells by combinatorial use of (i) an electric field and (ii) a agarose-patterned substrate within the electrochemical cell of the present invention is shown in FIG. 11.

7. Adaptations and Extensions of the Present Invention

The system, and method, of the present invention may be adapted, and extended, by any of (1) optimizing fluid composition for movement and viability, (2) development of a theoretical model to describe the observed responses and dependence on electrode composition/cell type/fluidic composition, (3) assessment of, and subsequent reference to, biological effects as are incurred responsively to field strength and duration, (4) exploration of protective aqueous additives, (5) exploration of the role of supplemental non-adhesive or adhesive coatings that may enhance patterning efficiency, and (6) manipulation of individual cell by the aid of the light by using opto-electrochemical system described earlier.

7.1 Patterning the Back Contact

With this approach the back contact of silicon substrate is patterned into small regions as illustrated in FIG. 12b. By applying potential to the desired location a circuit is completed and the cells or organic molecules will be patterned in this small selected region. On the other hand since the electrical circuit is not complete for the rest of the regions, there will not be a pattern formation. By adding a step of washing through a fluidic channel the cells that are not attached (attracted) to the electrodes will be removed. However, due to application of an electric field appearing at locations where cells are desired to remain, cells will indeed remain at these locations. By (i) repeated additions of new cell solution, (ii) repeated attraction of cells within the solutions to localized regions by application of an applied electric field followed by (iii) washing of the undesired cells away, one is permitted to form diverse different types of cell arrays on the same substrate. FIG. 12 illustrates this process, with the effect of a patterned back contact on the localized patterning of organic cells or molecules being shown in FIG. 12a.

7.2 Optical Manipulation of A Single Cell

It has been found that when light intensity is increased then the current at the anode became more cathodic. This phenomena can be beneficially used in the following way.

Cells or biological molecules can be patterned electrically on an agarose patterned substrate as discussed earlier. By approaching with a high intensity laser light the characteristics of the local electrochemical reactions can be changed. By making this localized region more cathodic, cells will be rejected from the electrode surface. Since light is shined to a very local area across the substrate this effect will occur only where the light is. The rest of the patterned cells on the substrate will not effected and will remain the same. In this way it is possible to remove a desired cell or biological molecule from a desired location among a larger population.

8. Applications of the Present Invention

The present invention has commercial applications in the assembly of both biological and non-biological structures.

Bio-application include cell-based biosensors, drug discovery, pharmacogenomics, functional genomics, high-throughput phenotyping, in vitro biology (combinatorial cell culture, signal transduction mechanisms), or any application requiring massive parallelism with biological cells. Biological cells of all types, specifically including plant, bacterial and animal cells—alone or in combination(s)—are manipulatable by the method and apparatus of the present invention.

Device applications included large array displays, massively parallel III–V and II–VI device integration on a different mother substrates, heterogeneous integration and pick and place of electronic and/or opto-electronic devices.

9. Recapitulation, and Summary

The viability of the integration of different non-biological and biological molecules (biomolecules), beads, pucks, microspheres cellular structures, cells and like small structures on different substrates has been shown.

With the system and method of the present invention economical, massively parallel, high-yield, and quick integration of devices is possible. Economical integration and/or assembly of very complex patterned devices is possible in the fabrication of diverse opto-electronic, electronic and biological devices.

The novel system and method of the present invention may in the future be expanded by, for example, the patterning of non-adhesive hydrogels, or by addressing with optical assistance.

The implications of the present invention are arguably quite profound. Even as presently configured and taught, the present invention is arguably a true paradigm-shift, permitting the modification and/or probing of live cells in parallel much the way that rapid-sequencing transformed the Human Genome Project.

Although specific embodiments of the invention have now be described with reference to the drawings, it should be understood that such embodiments are by way of example only and are merely illustrative of but a small number of the many possible specific embodiments to which the principles of the invention may be applied. Various changes and modifications obvious to one skilled in the art to which the invention pertains are deemed to be within the spirit, scope and contemplation of the invention as further defined in the appended claims.

In accordance with the preceding explanation, variations and adaptations of the electric-field-assisted fluidic assembly method, and apparatus, of the present invention will suggest themselves to a practitioner of any of the electrochemical, optics or biological arts. For example, the electrochemical cell may be extremely large, of meters in dimension, for the fluidic assembly of large devices, such as display screens.

In accordance with these and other possible variations and adaptations of the present invention, the scope of the invention should be determined in accordance with the following claims, only, and not solely in accordance with that embodiment within which the invention has been taught.

What is claimed is:

1. A method of assembling members of a group consisting of any of inorganic and bio-organic substances and molecules, and beads, pucks and other small things that are capable of holding an electrical charge, the method comprising:

photolithographically first-patterning a photosensitive electrode so that the electrode assumes first regions that are charged to a first electrical polarity and second regions that are charged to a second, opposite, electrical polarity; and second-patterning members selected from the group consisting of any of inorganic and bio-organic substances and molecules, and beads, pucks and other small things that are both (i) electrically charged to a first polarity, and (ii) immersed in a fluid transport medium that is upon the electrode, by moving under force of an electric field these members to charged second regions of the first-patterned electrode which second regions are of an opposite electrical polarity to the members;

wherein the members respond to the electric field and accumulate on, and assume the pattern of, the second regions.

2. The assembly method according to claim 1 wherein the second-patterning is of group members that are negatively charged while the patterned electrode second regions are positively charged.

3. The assembly method according to claim 1
wherein the second-patterning is of group members that are positively charged while the patterned electrode second regions are negatively charged.

4. The assembly method according to claim 1
wherein the second-patterning is of members selected from the group consisting of bio-organic substances and molecules.

5. The assembly method according to claim 1
wherein the second-patterning is of members selected from the group consisting of biological cells and components of biological cells.

6. The assembly method according to claim 5
wherein the components of biological cells are selected from the group consisting of bio-organic substances and molecules obtained from biological cells.

7. The assembly method according to claim 1
wherein the second-patterning is of members selected from the group consisting of live biological cells.

8. The assembly method according to claim 7
wherein the live biological cells are selected from the group consisting of plant cells, bacterial cells and animal cells.

9. The assembly method according to claim 1
wherein the second-patterning is of members selected from the group consisting of biological molecules.

10. The assembly method according to claim 9
wherein the second-patterning is of DNA.

11. The assembly method according to claim 9
wherein the second-patterning is of members selected from the groups consisting of proteins.

12. The assembly method according to claim 1
wherein the fluid transport medium is bio-compatible with the living bio-organic substances and molecules.

13. The assembly method according to claim 1 further comprising, at a time and as a step before the photolithographically first-patterning, the additional step of:
coating the photosensitive electrode with a non-stick substance to which bio-organic substances, molecules and/or cells subsequently applied in the second-patterning step will not stick;
wherein the photolithographically first-patterning of the electrode also serves to pattern the non-stick substance.

14. The assembly method according to claim 13,
wherein the coating of the photosensitive electrode is with agarose gel.

15. The assembly method according to claim 1
wherein the photosensitive electrode consists essentially of a semiconductor.

16. A method of assembling any of inorganic and bio-organic substances and molecules, and beads, pucks and other small things that are capable of holding an electrical charge, the method comprising:
first patterning a photosensitive electrode by selectively exposing it with masked radiation so as to pattern the electrode into first and second electrically charged regions;
placing any of inorganic and bio-organic substances and molecules, and beads, pucks and other small things that are electrically charged to an electrical polarity opposite to that of the second charged region within a fluid transport medium upon the first-patterned photosensitive electrode; and
imposing an electrical field across the fluid transport medium so that the electrically-charged inorganic and bio-organic substances and molecules, and beads, pucks and other small things that are within the fluid transport medium will migrate to the second charged region of the patterned photosensitive electrode, which region is of opposite polarity to the polarity of the electrically-charged inorganic and bio-organic substances and molecules, and beads, pucks and other small things;
wherein the inorganic and bio-organic substances and molecules, and beads, pucks and other small things assume the pattern of the photosensitive electrode second region that resulted from exposure of the photosensitive electrode with masked radiation.

17. A method of assembling small things that are capable of holding an electrical charge, the method comprising:
spacing parallel a semiconductor first electrode at a separation from a transparent second electrode;
photolithographically patterning with light transmitted through the transparent second electrode the semiconductor first electrode so that first regions of the first electrode are electrically charged to a first electrical polarity while second regions of the first electrode are electrically charged to a second, opposite, electrical polarity;
placing a liquid medium containing small things that are capable of holding an electrical charge between the first and the second electrode; and
electrically charging the small things to a first electrical polarity;
wherein the small things that are electrically charged to the first electrical polarity are electrically attracted to the second regions of the patterned photosensitive electrode that are charged to the second electrical polarity, and will thus assume the pattern of these second regions.

* * * * *